US00PP22706P3

(12) United States Plant Patent
Park

(10) Patent No.: US PP22,706 P3
(45) Date of Patent: May 1, 2012

(54) ***CALADIUM* PLANT NAMED 'SNOW WHITE PARK'**

(50) Latin Name: *Caladium humboldtii*
Varietal Denomination: SNOW WHITE PARK

(76) Inventor: Soon Kyo Park, Yongin-Si (KR)

( * ) Notice: Subject to any disclaimer, the term of this patent is extended or adjusted under 35 U.S.C. 154(b) by 0 days.

(21) Appl. No.: 12/803,733

(22) Filed: Jul. 1, 2010

(65) Prior Publication Data

US 2012/0005794 P1 Jan. 5, 2012

(51) Int. Cl.
*A01H 5/00* (2006.01)

(52) U.S. Cl. ..... Plt./373
(58) Field of Classification Search ..... Plt./373
See application file for complete search history.

(56) References Cited

OTHER PUBLICATIONS

UPOVROM Plant Variety Database 2011/03. p. 1.*

* cited by examiner

*Primary Examiner* — Annette Para
(74) *Attorney, Agent, or Firm* — Cassandra Bright

(57) ABSTRACT

A new and distinct *Caladium* cultivar named 'SNOW WHITE PARK' is disclosed, characterized by distinctive white foliage with green veins and margins, and a compact, very short plant habit. The new variety is a *Caladium,* normally produced as an indoor ornamental plant.

1 Drawing Sheet

Latin name of the genus and species: *Caladium humboldtii.*
Variety denomination: 'SNOW WHITE PARK'.

BACKGROUND OF THE INVENTION

The new cultivar was discovered as a spontaneous whole plant mutation by the inventor, Soonkyo Park, a citizen of South Korea. The parent variety is the unpatented variety *Caladium humboldtii.* The new variety was discovered April 2003, by the inventor in a commercial planting of *Caladium humboldtii* in Gyeonggi-do, South Korea.

Asexual reproduction of the new cultivar 'SNOW WHITE PARK' by tissue culture was first performed July 2003, at a commercial laboratory in Gyeonggi-do, South Korea. Many generations have since been produced and have shown that the unique features of this cultivar are stable and reproduced true to type on successive generations.

SUMMARY OF THE INVENTION

The cultivar 'SNOW WHITE PARK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SNOW WHITE PARK' These characteristics in combination distinguish 'SNOW WHITE PARK' as a new and distinct *Caladium* cultivar:

1. Distinctive white leaves with green veins and green margins.
2. Compact and short plant form.

PARENT COMPARISON

Plants of the new cultivar 'SNOW WHITE PARK' are similar to plants of the parent, *Caladium humboldtii* in most horticultural characteristics, however, plants of the new cultivar 'SNOW WHITE PARK' are shorter. Additionally, foliage of the parent variety is light green with green speckles and green veins, whereas 'SNOW WHITE PARK' has white foliage with green veins

COMMERCIAL COMPARISON

The parent variety is the best commercial comparison to the new cultivar.

BRIEF DESCRIPTION OF THE PHOTOGRAPH

The accompanying photograph in FIG. 1 illustrates in full color a typical plant of 'SNOW WHITE PARK' grown in a greenhouse, in Gyeonggi-do, South Korea, in a commercial 11 cm container. Age of the plant photographed is approximately 8 months from a stage three tissue culture plant. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SNOW WHITE PARK' plants grown during the winter months in a greenhouse in Gyeonggi-do, South Korea. The growing temperature ranged between 20° C. to 30° C. daytime and 18° to 20° C. at night. Measurements and numerical values represent averages of typical plant types.

Botanical classification: *Caladium humboldtii* 'SNOW WHITE PARK.'

PROPAGATION

Time to initiate roots: Summer: 10 to 15 days at approximately 25° C. Winter: 15 to 20 days at approximately 25° C.

Root description: Roots thin, moderately fibrous, non-fleshy, moderately densely branched. Colored near RHS White 155A.

Tuber description: No tubers present, only roots

PLANT

Growth habit: Upright and outwardly arching, leaves emerging basally.

Pot size of plant described: 10 cm

Height: Approximately 8.6 cm to top of leaf plane from soil level

Plant spread: Approximately 18.0 cm

Growth rate: Moderate

Main stem color: No stems present; leaves (on petioles) grow directly from the base (soil.)

Branching characteristics: No lateral branches

FOLIAGE

Leaf:

*Arrangement.*—Alternate; growing directly from the base (soil).

*Quantity.*—Approximately 55 per plant.

*Average length.*—5.8 cm.

*Average width.*—3.3 cm.

*Shape of blade.*—Ovate.

*Apex.*—Acute with a short mucronulate tip.

*Base.*—Cordate.

*Margin.*—Entire.

*Texture of top surface.*—Smooth, dull.

*Pubescence.*—No leaf pubescence.

*Aspect.*—Leaves placed horizontal to slightly drooping in an average angle of 30° (0°=horizontal).

*Color.*—Young foliage upper side: Near RHS Greyed-Green 191 C to 192A, both colors present. Margins darker; RHS Green N137A. Young foliage under side: Near RHS Green 143D and Yellow-Green 144D, both colors present. Mature foliage upper side: Near RHS White 155C, margins near Green 137A. Mature foliage under side: Near RHS White 155C, margins near Green 143A.

*Venation.*—Type: Pinnate. Venation color upper side: Near RHS Green 137A. Venation color under side: Near RHS Green 143A.

*Petiole.*—Length: Approximately 10.9 cm. Diameter: Approximately 0.15 cm. Color: Near RHS Yellow-Green 148B, dotted with Yellow-Green 147A, distal part near RHS Yellow-Green 146C, basal part near RHS Grey-Green 193A, 193B and 193C, all colors present. Texture: Smooth, slightly glossy.

*Petiole sheath.*—No petiole sheaths present.

*Cataphylls.*—Present: Cataphylls not present.

*Geniculum or wing.*—Present: No geniculum present, wing is described here: Shape: Narrow triangular. Length: Approximately 2.2 cm. Diameter: Approximately 0.1 cm. Color: Near RHS Greyed-Green 192B. Other Features: No other features.

FLOWER

No flowers present, flowering not observed to date.

OTHER CHARACTERISTICS

Seeds and fruits: Not observed to date.

Disease/pest resistance: Neither resistance nor susceptibility to pathogens and pests common to *Caladium* have been observed.

Temperature tolerance: The new variety tolerates temperatures between 13° C. to 40° C.

What is claimed is:

1. A new and distinct cultivar of *Caladium* plant named 'SNOW WHITE PARK' as herein illustrated and described.

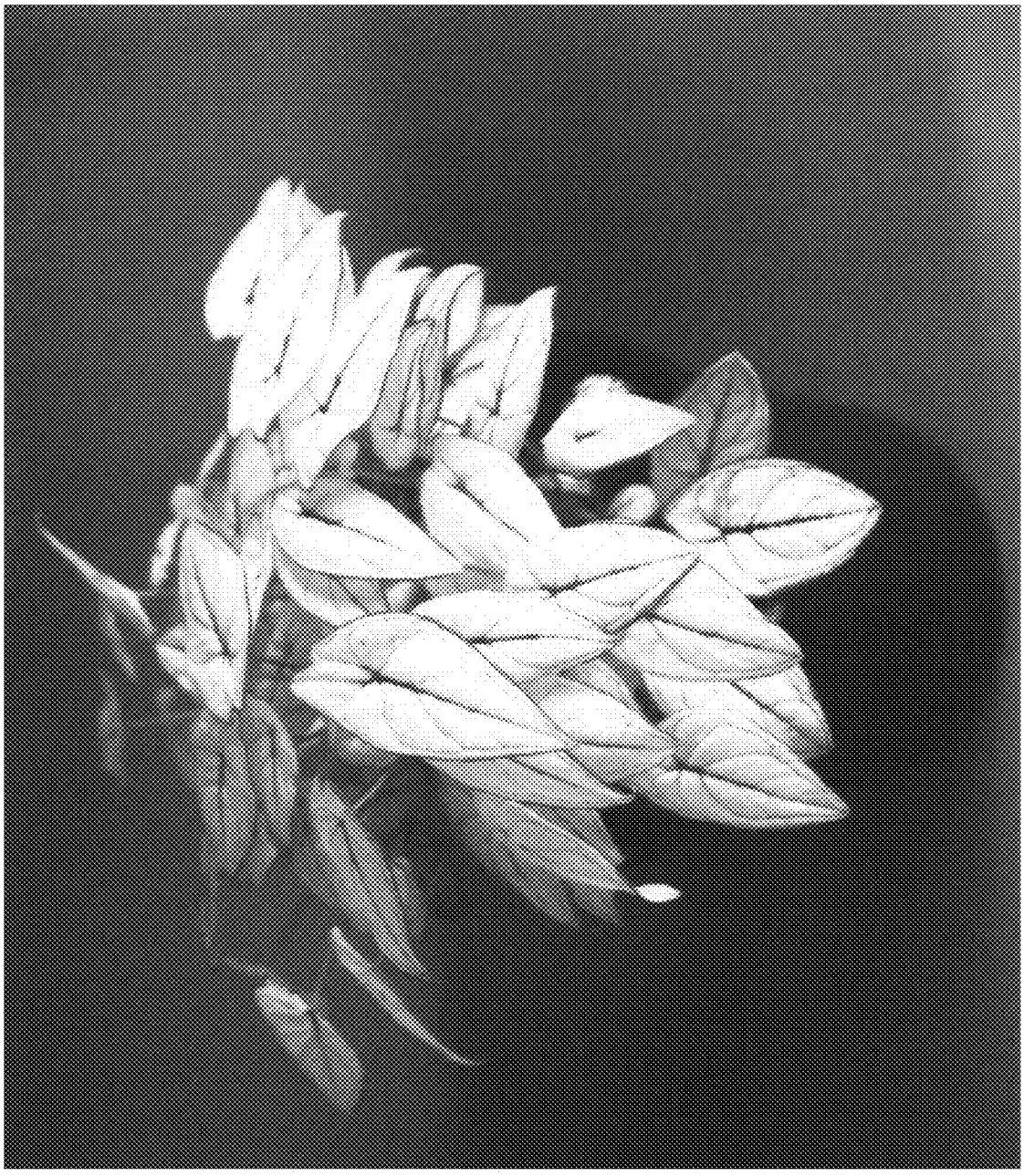

* * * * *